United States Patent [19]

Hisamoto et al.

[11] Patent Number: 4,511,733
[45] Date of Patent: Apr. 16, 1985

[54] FLUORINE-CONTAINING AMINOCARBOXYLIC ACID COMPOUNDS

[75] Inventors: Iwao Hisamoto, Suita; Chiaki Maeda, Kyoto; Masaru Hirai, Settsu, all of Japan

[73] Assignee: Daikin Kogyo Co., Ltd., Osaka, Japan

[21] Appl. No.: 452,811

[22] Filed: Dec. 23, 1982

[30] Foreign Application Priority Data

Dec. 25, 1981 [JP] Japan ................... 56-210363

[51] Int. Cl.³ ............................ C07C 101/30
[52] U.S. Cl. .................. 560/253; 260/501.11; 562/567; 252/3
[58] Field of Search ............... 562/574, 567; 560/252, 560/253; 260/501.11

[56] References Cited

U.S. PATENT DOCUMENTS 3,755,435  8/1973  Sundby ........................ 562/567
4,351,954  9/1982  Muramatsu ..................... 562/574

FOREIGN PATENT DOCUMENTS 56-55359    5/1981   Japan ........................ 562/574
56-164151  12/1981   Japan ........................ 562/574
57-46948    3/1982   Japan ........................ 562/567
57-46949    3/1982   Japan ........................ 562/567

*Primary Examiner*—Michael L. Shippen
*Attorney, Agent, or Firm*—Birch, Stewart, Kolasch & Birch

[57] ABSTRACT

A fluorine-containing aminocarboxylic acid compound of the formula:

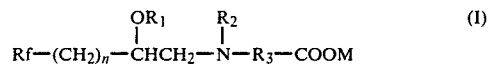

$$Rf-(CH_2)_n-CHCH_2-N-R_3-COOM \quad (I)$$
with $OR_1$ on the CH and $R_2$ on the N wherein Rf is a $C_3-C_{21}$ fluorine-containing aliphatic group; $R_1$ is a hydrogen atom or a $C_1-C_3$ acyl group; $R_2$ is a hydrogen atom or a $C_1-C_5$ alkyl group; $R_3$ is a substituted or unsubstituted $C_1-C_3$ alkylene group; M is a cation; and n is an integer of 1 to 5 effectively lowers the surface tension of water and/or organic liquids and the interfacial tensions between them.

6 Claims, No Drawings

FLUORINE-CONTAINING AMINOCARBOXYLIC ACID COMPOUNDS

This invention relates to novel fluorine-containing compounds, and their preparation and use. More particularly, it relates to aminocarboxylic acid compounds having a fluorine-containing group, a process for preparing the aminocarboxylic acid compounds and a surface-tension lowering agent for water and/or organic liquids comprising the aminocarboxylic acid compound.

A fluorine-containing compound which effectively lowers the surface tension of water and of various organic liquids is used, for example, as an additive for a foam fire-extinguisher, a penetrating agent and a leveling agent for resinous materials.

However, conventional anionic fluorine-containing compounds (surfactants) which greatly lower the surface tension of water do not efficiently lower the surface tension of organic liquids such as ethylene glycol, methyl ethyl ketone and dimethylformamide. Thus, an anionic fluorine-containing compound which can lower the surface tension of organic liquids as well as that of water was not known, and its appearance has been highly desired.

As a result of an extensive study, it has now been found that a fluorine-containing aminocarboxylic acid compound of the formula:

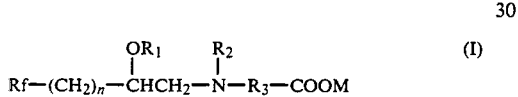

wherein Rf is a $C_3$-$C_{21}$ fluorine-containing aliphatic group; $R_1$ is a hydrogen atom or a $C_1$-$C_3$ acyl group; $R_2$ is a hydrogen atom or a $C_1$-$C_5$ alkyl group; $R_3$ is a substituted or unsubstituted $C_1$-$C_3$ alkylene group; M is a cation; and n is an integer of 1 to 5 effectively lowers the surface tension of water and/or organic liquids.

In the formula (I), Rf may be a saturated or unsaturated, straight or branched, substituted or unsubstituted fluorine-containing aliphatic group and may have an oxygen atom(s) in the main chain. Preferably, Rf has 3 to 21 carbon atoms and/or bears a greater number of fluorine atoms than that of carbon atoms. $R_1$ is a hydrogen atom or a $C_1$-$C_3$ acyl group. The acyl group may be lower alkanoyl such as formyl, acetyl or propionyl. $R_2$ is a hydrogen atom or a $C_1$-$C_5$ alkyl group. The alkyl group may be methyl, ethyl, propyl, butyl, pentyl, etc. $R_3$ is a substituted or unsubstituted $C_1$-$C_3$ alkylene group. The alkylene group may be methylene, ethylene or propylene. M is a cation such as an alkali metal ion, an ammonium ion, an N-substituted ammonium ion (e.g. $H^+$, $Na^+$, $K^+$, $Li^+$, $NH_4^+$, $NH_3(CH_2)_2OH$, $NH_4(CH_3)_2$, $NH(C_2H_5)_3$).

Specific examples of the compound (I) are as follows:

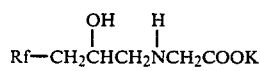

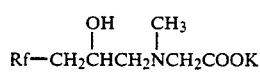

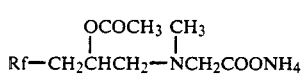

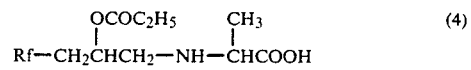

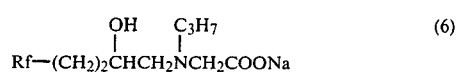

Rf in these compounds represents preferably $C_8F_{17}-$, $C_9F_{19}-$, $H(C_{10}F_{20})-$,

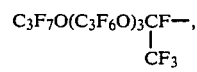

$C_{10}F_{19}-$ or $C_9F_{17}-$.

The fluorine-containing aminocarboxylic acid compound (I) of the invention may be prepared by reacting a fluorine-containing epoxide of the formula:

wherein Rf and n are each as defined above with a compound of the formula:

wherein $R_2$, $R_3$ and M are each as defined above.

The reaction can be carried out, if desired, in the presence of an inert solvent (e.g. methanol, isopropanol, methyl ethyl ketone, tetrahydrofuran, etc.) or a mixture of the inert solvent and water at a temperature of from 20° to 150° C., preferably from 40° to 100° C., with stirring for 3 to 10 hours, preferably for 5 to 8 hours. The reaction is usually carried out in the absence of a catalyst; but, if neccessary, a catalyst such as pyridine and tertiary amines may be employed. The compound (I) wherein $R_1$ is an acyl group is prepared, for example, by reacting the compound (I) wherein $R_1$ is a hydrogen atom which is obtained by the above described process with an acid halide or an acid anhydride.

Since the fluorine-containing compound (I) of the invention is highly effective in lowering the surface tension of water and/or organic liquids and the interfacial tensions between them, it may be used as an additive for fire-extinguishers (e.g. aqueous film foam fire-extinguishers, synthetic surfactant fire-extinguishers, protein foam fire-extinguishers, powder fire-extinguishers), a leveling agent for waxes and paints, a penetrating agent for fibercoloring liquids, metal processing solutions and photographic processing solutions, etc. Further, it may be used as a stripping or releasing agent for resins or as an emulsifier in polymerization.

The amount of the fluorine-containing compound (I) to be used varied widely with the purpose but may be usually from 0.001 to 5% by weight, preferably from 0.001 to 2% by weight on the basis of the weight of the base material.

The present invention will be illustrated further in detail by the following Examples wherein % is by weight.

EXAMPLE 1

Preparation of $C_9F_{19}CH_2CH(OH)CH_2N(CH_3)CH_2COOK$

Into a 100 ml volume four-necked flask equipped with a thermometer, a condenser and a stirrer,

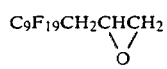

(10 g, 0.019 mol), potassium sarcosine (2.4 g, 0.019 mol) isopropanol (15 g) and water (30 g) were charged and stirred for 6 hours on a water bath maintained at 50° C. Complete consumption of the epoxide compound was ascertained by gas chromatographic analysis.

From the reaction mixture, isopropanol and water were evaporated off, and thereafter the residue was washed with an excess amount of a mixed solvent of acetonitrile and trichlorotrifluoroethane (50:50 by weight) to give a solid product (11.5 g). Yield: 93%. M.P. 92°-94° C.

The product was identified as the entitled compound by H- and F-NMR. The results are shown in Tables 1 and 2 respectively.

TABLE 1

| Chemical shift δ (ppm) | Characteristic group | Signal intensity |
|---|---|---|
| 2.27 | $CF_2$—$CH_2$— | 2H |
| 2.34 | N—$CH_3$ | 3H |
| 2.50 | CH—$CH_2$—N | 1H |
| 2.58 | | 1H |
| 3.08 | $CH_2COO$ | 2H |
| 4.19 | O<br>\|<br>CH— | 1H |
| 4.83 | C—OH($+H_2O$) | 1H |

TABLE 2

| Chemical shift δ (ppm) | Signal intensity |
|---|---|
| −5.0 | 6F |
| 34.9 | 2F |
| 37.3 | 2F |
| 43.5 | 2F |
| 44.0 | 4F |
| 45.9 | 2F |
| 108.6 | 1F |

From the results shown in Table 1, the presence of a perfluoroalkyl group having 19 fluorine atoms was ascertained.

EXAMPLE 2

Preparation of $C_9F_{19}CH_2CH(OH)CH_2NHCH_2COOK$

In the same manner as in Example 1 but using potassium glycine (2.2 g) in place of potassium sarcosine and taking a reaction time of 5 hours, the reaction was effected to give a solid compound (11.7 g). Yield: 96%, M.P. >200° C. The product was identified as in Example 1. The results of F-NMR were substantially the same as those in Table 2. The results of H-NMR are shown in Table 3.

TABLE 3

| Chemical shift δ (ppm) | Characteristic group | Signal intensity |
|---|---|---|
| 2.30 | $CF_2$—$CH_2$— | 2H |
| 4.71 | N—H | 1H |
| 2.63 | CH—$CH_2$—N | 1H |
| 2.77 | | 1H |
| 3.24 | $CH_2$—COO | 2H |
| 4.20 | O<br>\|<br>CH— | 1H |
| 4.71 | C—OH($+H_2O$) | 1H |

EXAMPLE 3

Surface tension of a 0.3% aqueous solution or 0.3% ethylene glycol solution of each compound shown in Table 4 was measured at 25° C. by the Wilhelmy method. The results are shown in Table 4.

TABLE 4

| | Surface tension (dyn/cm) | |
|---|---|---|
| Compound | Aqueous solution | Ethylene glycol solution |
| Compound (1) Rf = $C_9F_{19}$ | 21.3 | 22.9 |
| Compound (2) Rf = $C_9F_{19}$ | 15.4 | 17.2 |
| Compound (3) Rf = $C_8F_{17}$ | 15.2 | 17.3 |
| Compound (5) Rf = $C_8F_{17}$ | 16.5 | 17.0 |
| Comparative Example*[1] | 72.0 | 47.7 |

Note:
*[1] Containing no surfactant.

What is claimed is:

1. A fluorine-containing aminocarboxylic acid compound of the formula:

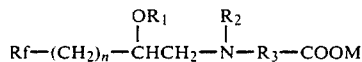

wherein Rf is a $C_3$–$C_{21}$ fluorine-containing aliphatic group bearing a greater number of fluorine atoms than that of carbon atoms or a $C_3$–$C_{21}$ aliphatic group bearing a greater number of fluorine atoms than that of carbon atoms which has up to four oxygen atoms in the main chain; $R_1$ is a hydrogen atom or a $C_1$–$C_3$ alkanoyl; $R_2$ is a hydrogen atom or a $C_1$–$C_5$ alkyl group; $R_3$ is a $C_1$–$C_3$ alkylene group; M is a member selected from the group consisting of a proton, an alkali metal ion, an ammonium ion, $NH_3(CH_2)_2OH$, $NH_2(CH_3)_2$, and $NH(C_2H_5)_3$; and n is an integer of 1 to 5, said compound being useful as a surface tension lowering agent for water and/or organic liquids.

2. The compound according to claim 1, wherein Rf is an aliphatic group selected from the group consisting of $C_8C_{17}$—, $C_9F_{19}$—, $H(C_{10}F_{20})$—,

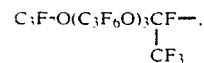

$C_{10}F_{19}$— and $C_9F_{17}$—.

3. The compound according to claim 1 wherein $R_1$ is a hydrogen atom.

4. The compound according to claim 1 wherein $R_1$ is a $C_1$–$C_3$ alkanoyl.

5. The compound according to claim 1 wherein $R_2$ is a hydrogen atom.

6. The compound according to claim 1 wherein $R_2$ is a $C_1$–$C_5$ alkyl group.

* * * * *